(12) United States Patent
Ko

(10) Patent No.: US 12,133,675 B2
(45) Date of Patent: *Nov. 5, 2024

(54) TREATMENT APPARATUS AND METHOD OF CONTROLLING SAME

(71) Applicant: LUTRONIC CORPORATION, Goyang (KR)

(72) Inventor: Kwang Chon Ko, Paju (KR)

(73) Assignee: LUTRONIC CORPORATION, Goyang (KR)

( * ) Notice: Subject to any disclaimer, the term of this patent is extended or adjusted under 35 U.S.C. 154(b) by 418 days.

This patent is subject to a terminal disclaimer.

(21) Appl. No.: 17/572,427

(22) Filed: Jan. 10, 2022

(65) Prior Publication Data

US 2022/0125502 A1 Apr. 28, 2022

Related U.S. Application Data

(63) Continuation of application No. 16/066,952, filed as application No. PCT/KR2018/002563 on Mar. 5, 2018, now Pat. No. 11,241,278.

(30) Foreign Application Priority Data

Mar. 6, 2017 (KR) .......................... 10-2017-0028121

(51) Int. Cl.
*A61B 18/12* (2006.01)
*A61B 18/14* (2006.01)
*A61B 18/00* (2006.01)

(52) U.S. Cl.
CPC ...... *A61B 18/1477* (2013.01); *A61B 18/1206* (2013.01); *A61B 2018/00059* (2013.01);
(Continued)

(58) Field of Classification Search
CPC ............ A61B 18/1477; A61B 18/1206; A61B 2018/00059; A61B 2018/00696; A61B 2018/00916
See application file for complete search history.

(56) References Cited

U.S. PATENT DOCUMENTS

2002/0058936 A1* 5/2002 Avrahami .............. A61N 1/327
604/20
2006/0264926 A1 11/2006 Kochamba
(Continued)

FOREIGN PATENT DOCUMENTS

JP 201183484 A 4/2011
KR 1020100098707 A 9/2010
(Continued)

*Primary Examiner* — Daniel W Fowler

(57) ABSTRACT

The present invention relates to a treatment apparatus and a method of controlling the same. There are provided a treatment apparatus, including a handpiece, an RF generator generating RF energy, an insertion unit configured to advance and retract toward one direction of the handpiece, selectively inserted into a tissue, and electrically connected to the RF generator to transfer the RF energy to the inside of the tissue, and a substance storage unit receiving a therapeutic substance therein and detachably installed on one side of the handpiece to transfer the substance to the inside of the tissue by the advancing operation of the insertion unit and a method of controlling the same.

15 Claims, 10 Drawing Sheets

(52) U.S. Cl.
　　　CPC ............... *A61B 2018/00696* (2013.01); *A61B 2018/00916* (2013.01)

(56) References Cited

U.S. PATENT DOCUMENTS

| | | |
|---|---|---|
| 2008/0294157 A1 | 11/2008 | Hosier |
| 2009/0187167 A1 | 7/2009 | Sexton et al. |
| 2011/0092883 A1 | 4/2011 | Uchiyama |
| 2012/0191091 A1 | 7/2012 | Allen |
| 2013/0197484 A1 | 8/2013 | Seddon et al. |
| 2014/0194789 A1 | 7/2014 | Ko |

FOREIGN PATENT DOCUMENTS

| | | |
|---|---|---|
| KR | 1020110000790 A | 1/2011 |
| KR | 1020110120166 A | 11/2011 |
| KR | 1020150014441 A | 2/2015 |
| KR | 1020150141256 A | 12/2015 |
| WO | WO2013164996 A1 | 11/2013 |

\* cited by examiner

TREATMENT APPARATUS AND METHOD OF CONTROLLING SAME

CROSS-REFERENCE TO RELATED APPLICATIONS

The present application is a continuation application of U.S. application Ser. No. 16/066,952 filed Jun. 28, 2018, which is a U.S. National Stage of PCT/KR2018/002563, filed Mar. 5, 2018, which claims the priority benefit of Korean Patent Application No. 10-2017-0028121, filed on Mar. 6, 2017 in the Korean Intellectual Property Office, the disclosures of which are incorporated herein by reference.

TECHNICAL FIELD

The present invention relates to a treatment apparatus and a method of controlling the same and, more particularly, to a treatment apparatus in which an insertion unit is inserted into a tissue and delivers RF energy and a method of controlling the same.

BACKGROUND ART

A method of treating a tissue may be divided into a method of treating a tissue outside the tissue and an invasive treatment method of treating a tissue by inserting some of or the entire treatment apparatus into the tissue. The invasive treatment method basically uses a treatment apparatus having a thin-necked insertion unit, such as a needle or a catheter. Treatment is performed after the treatment apparatus is inserted up to a target location within a tissue.

The invasive treatment method includes various treatment behaviors of performing treatment through a mechanical operation in the state in which a specific tissue within a tissue is touched or delivering energy to a target location within a tissue. Specifically, in addition to surgical treatment, the invasive treatment method is recently used for skin lesion treatment, such as wrinkle removal, scar removal and acne treatment, by inserting an insertion unit into the skin and delivering RF energy. Such a treatment method has been disclosed in Korean Patent Application Publication No. 10-2011-0000790.

The invasive treatment method includes a picky process of inserting the insertion unit into a tissue and involves pain, but has an advantage in that a treatment effect is excellent because treatment is directly performed within a tissue. Accordingly, various research and development for performing complex treatment within a tissue in the state in which the insertion unit has been inserted are carried out.

DISCLOSURE

Technical Problem

An object of the present invention is to provide a treatment apparatus capable of performing treatment by combining a treatment method of transferring RF energy to a tissue and a treatment method of transferring a therapeutic substance in performing treatment using an invasive treatment method, and a method of controlling the same.

Technical Solution

A treatment apparatus according to the present invention provides a treatment apparatus, including a handpiece, an RF generator generating RF energy, an insertion unit configured to advance and retract toward one direction of the handpiece, selectively inserted into a tissue, and electrically connected to the RF generator to transfer the RF energy to the inside of the tissue, and a substance storage unit receiving a therapeutic substance therein and detachably installed on one side of the handpiece to transfer the substance to the inside of the tissue by the advancing operation of the insertion unit.

In this case, the substance storage unit may be positioned on a path along which the insertion unit moves while the insertion unit performs the advancing and retracting operation. The insertion unit may be inserted into the tissue through the substance storage unit when performing the advancing operation.

The insertion unit is inserted into the tissue in the state in which the substance has been applied on an external surface of the insertion unit while the insertion unit penetrates the substance storage unit. Accordingly, the substance may be transferred from a surface of the tissue to the depth into which the end of the insertion unit is inserted along the path formed within the tissue by the insertion of the insertion unit. Furthermore, the insertion unit may operate to transfer the RF energy after the substance is transferred to the inside of the tissue.

In one embodiment, an external surface of the insertion unit may have a structure in which prominences and depressions are formed in order to improve transfer efficiency of the substance to the inside of the tissue.

Meanwhile, the treatment apparatus further includes a controller controlling the operations of the RF generator and the insertion unit. The controller may differently control the advancing and retracting operation of the insertion unit depending on whether the substance storage unit has been installed.

Specifically, the treatment apparatus further includes an installation sensing unit sending whether the substance storage unit has been installed. The controller may differently control the advancing and retracting operation of the insertion unit based on information sensed by the installation sensing unit.

Furthermore, the controller may control the advancing and retracting operation of the insertion unit in a first mode in the state in which the substance storage unit has not been installed. The controller may control the advancing and retracting operation of the insertion unit in a second mode in the state in which the substance storage unit has been installed.

For example, if the depth of the same tissue is a target location, in the second mode, the insertion unit may be controlled to additionally advance as much as a length corresponding to a thickness of the substance storage unit compared to the first mode.

Alternatively, in the first mode, the end of the insertion unit may be controlled to be inserted into the tissue when the insertion unit advances, and the end of the insertion unit may be controlled to be received within the handpiece when the insertion unit retracts. In the second mode, the end of the insertion unit may be controlled to be inserted into the tissue when the insertion unit advances, and the end of the insertion unit may be controlled to be received within the substance storage unit when the insertion unit retracts.

The substance received in the substance storage unit may have a gel form. Furthermore, at least one surface of the substance storage unit through which the insertion unit penetrates may have a membrane structure having viscoelasticity so that the advancing and retracting operation of the insertion unit are easily performed and a leakage of the substance through a through hole formed by the advancing and retracting operation of the insertion unit is minimized. Moreover, the substance storage unit may further include a marking part indicating whether the substance storage unit is used when the substance storage unit is coupled to the handpiece.

Meanwhile, the present invention provides a method of controlling a treatment apparatus, including the steps of installing a substance storage unit in which a therapeutic substance is received on one side of a handpiece, advancing a plurality of insertion units to a substance storage unit so that the substance is applied on external surfaces of the insertion units provided in the handpiece, inserting the insertion units applied with the substance into a tissue by advancing the insertion units through a surface of the tissue, transferring RF energy to the inside of the tissue through the insertion units, and retracting the insertion units so that the insertion units exit from the tissue.

Moreover, the method of controlling a treatment apparatus may further include the step of sensing whether the substance storage unit has been installed.

In this case, the step of retracting the insertion units may further include the steps of retracting the insertion units so that the ends of the insertion units are located within the substance storage unit and inserting the insertion units into the tissue by moving the position of the handpiece in the state in which the ends of the insertion units have been positioned in the substance storage unit.

Furthermore, the present invention provides a method of controlling a treatment apparatus, including the steps of sensing whether an accommodation unit in which a therapeutic substance is received has been positioned on one side of a handpiece to which an insertion unit advances, setting the insertion unit in a first mode in which the insertion unit is advanced as much as a first length and transfers RF energy when the substance storage unit is sensed to have not been installed, and setting the insertion unit in a second mode in which the insertion unit is advanced as much as a second length longer than the first length and transfers RF energy when the substance storage unit is sensed to have been installed.

Moreover, the present invention may provide a treatment method using a treatment apparatus, including the steps of installing a substance storage unit in which a therapeutic substance is received on one side of the handpiece through which an insertion unit advances and retracts, advancing the insertion unit to the substance storage unit and applying the substance on an external surface of the insertion unit, inserting the insertion unit applied with the substance into a tissue and transferring the substance to the inside of the tissue, and transferring RF energy to the inside of the tissue using the insertion unit.

Advantageous Effects

In accordance with the present invention, there are advantages in that the time taken for treatment can be reduced, a treatment operation can be simplified, and a treatment effect can be improved because treatment of a method of transferring RF energy and treatment of a method of transferring a substance can be performed through a single operation.

MODE FOR INVENTION

Hereinafter, a treatment apparatus according to embodiments of the present invention is described in detail with reference to the drawings. In the following description, the location relations between elements are described in principle based on the drawings. Furthermore, the drawings may be enlarged and shown in order to simplify the structure of the invention for convenience of description or if necessary. Accordingly, the present invention is not limited thereto, and various devices may be added, changed or omitted.

Hereinafter, the "treatment apparatus" includes all apparatuses for treating mammals including people. The treatment apparatus may include may include various treatment apparatuses used to improve a lesion or the state of a tissue. For example, the treatment apparatus includes an apparatus transferring treating substances, such as medicines, anesthetic, and stem cells, an operation apparatus for surgically treating a specific tissue, and various treatment apparatuses transferring RF energy.

Hereinafter, a "tissue" means a set of cells forming various body organs of an animal including people, and includes various tissues forming various organs within the body, including a skin tissue.

Hereinafter, an "insertion unit" means an element that belongs to a treatment apparatus and that is inserted into a tissue. The insertion unit has a lengthy structure having a sharp and thin end, such as a needle, micro needle or a catheter, and includes various structures inserted into a tissue through a surface of the tissue.

Figure 1:
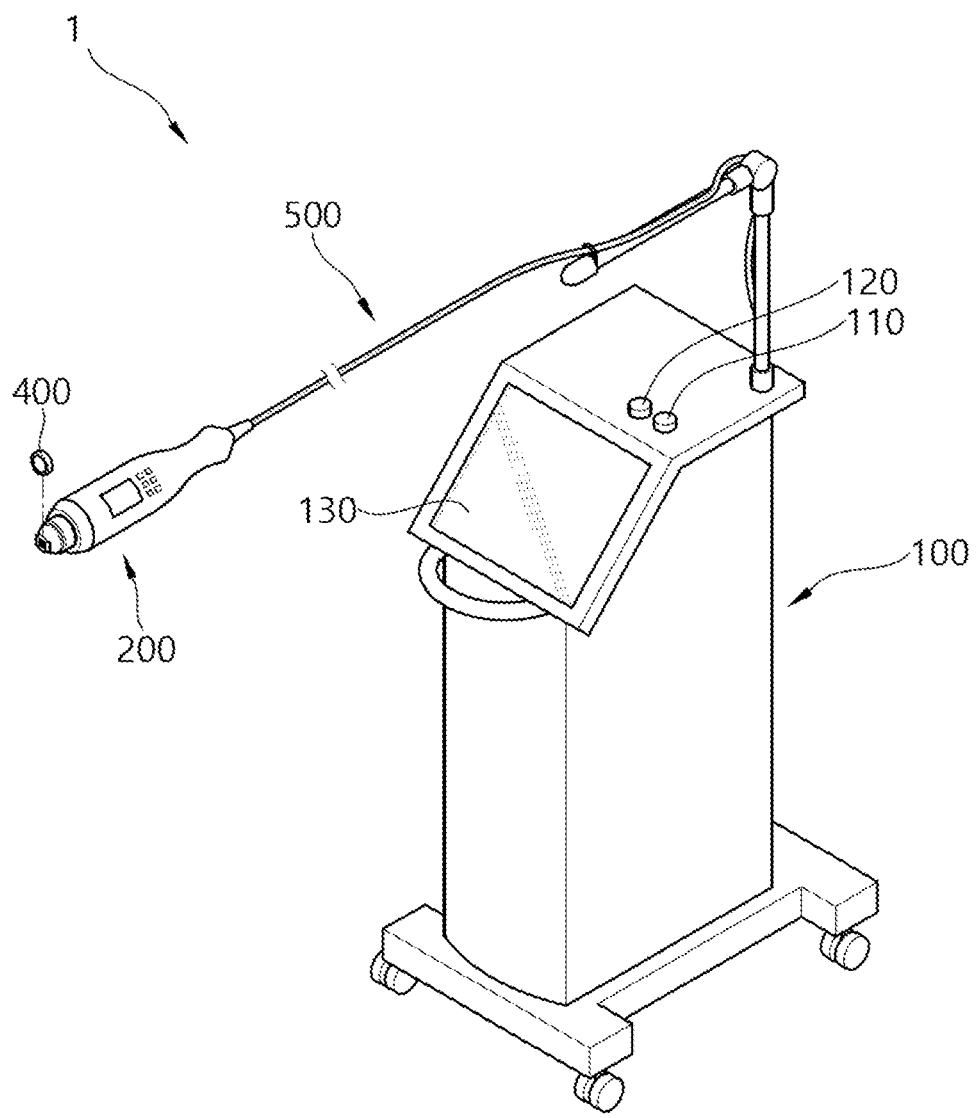
FIG. 1 is a perspective view showing a treatment apparatus according to an embodiment of the present invention.
Figure 2:
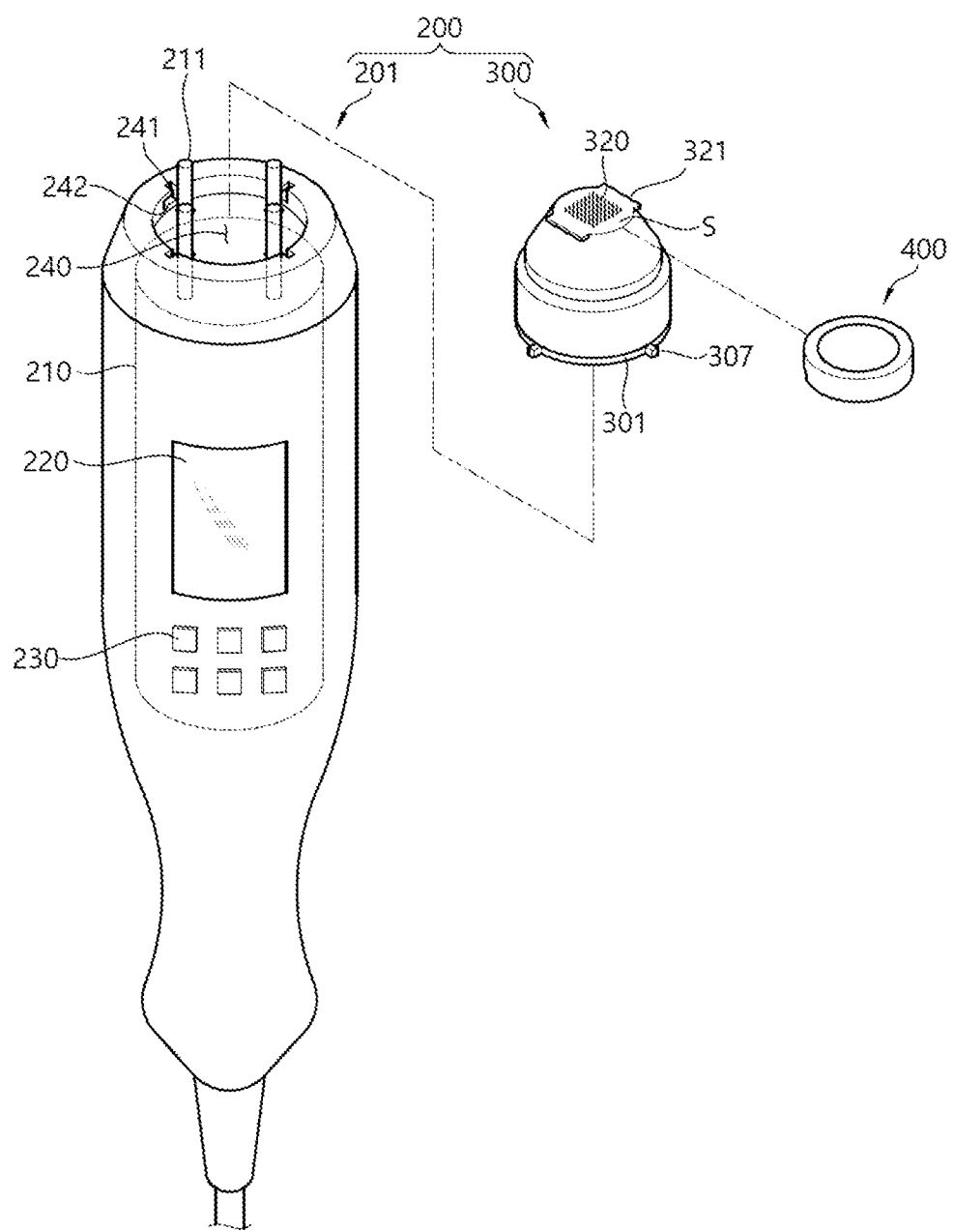
FIG. 2 is a perspective view showing the handpiece and substance storage unit of the treatment apparatus of FIG. 1.

Hereinafter, the treatment apparatus according to an embodiment of the present invention is described with reference to FIG. 1. FIG. 1 is a perspective view showing a treatment apparatus according to an embodiment of the present invention. FIG. 2 is a perspective view showing the handpiece and substance storage unit of the treatment apparatus of FIG. 1.

As shown in FIG. 1, the treatment apparatus 1 according to the present invention is configured to include a main body 100, a handpiece 200 enabling a user to perform treatment while the user graphs the handpiece, and a substance storage unit 400 detachably installed on one side of the handpiece.

An RF generator 140 (refer to FIG. 7) may be provided within the main body 100. The RF generator generates RF energy used for treatment. The frequency of RF energy generated from the RF generator may be controlled depending on the physical constitution, treatment purpose, a treatment portion, etc. of a patient. For example, RF energy used for skin treatment may be controlled in the range of 0.1 to 0.8 MHz.

A power on/off switch 110, a frequency control lever 120 capable of controlling the frequency of RF energy generated from the RF generator, and a touch screen 130 displaying a variety of types of information including operation contents of the treatment apparatus, enabling a user to enter commands, and displaying treatment information may be positioned on an external surface of the main body 100.

Meanwhile, the handpiece 200 is connected to the main body by a connection unit 500. The connection unit 500 is an element for transferring power necessary for various devices of the handpiece 200 to operate or a control signal from the main body. RF energy from the RF generator of the main body 100 may also be transferred to the insertion unit 320 of the handpiece through the connection unit 500. The connection unit 500 may consist of a cable including various signal lines, power lines, etc. or may consist of a bending structure that may be easily bent by a manipulation of a user.

The handpiece 200 is an element that substantially performs treatment at a location neighboring a treatment location in the treatment apparatus 1, and has a form capable of being grasped and used by a hand of a user. Schematically, the handpiece 200 is configured to include the insertion unit 320 configured to be inserted into a tissue and perform invasive treatment, a driving unit 210 for moving the insertion unit, and a handpiece manipulation unit 230 for manipulating the operation contents of the insertion unit and the driving unit.

Specifically, the handpiece manipulation unit 230 and a handpiece display unit 220 may be provided on an external surface of a housing forming the body of the handpiece 200. The handpiece manipulation unit 230 is configured to manipulate the on/off of the handpiece, control the insertion depth of the insertion unit or the amount of energy transferred through the insertion unit. The handpiece display unit 220 may display a set mode or a variety of types of information necessary during treatment for a user. Accordingly, the user can easily manipulate treatment contents during treatment through the handpiece manipulation unit 230 in the state in which the user has grasped the handpiece 200 with a hand, and may easily check treatment contents through the handpiece display unit 220.

The driving unit 210 is positioned within the handpiece 200. The driving unit 210 is configured to linearly move an output terminal 211 provided on one side of the driving unit in the length direction. A plurality of needles corresponding to the insertion unit 320 is disposed at the end of the output terminal. When the output terminal 211 linearly moves, the insertion unit 320 may advance and retract to and from one side of the handpiece. As described above, the insertion unit 320 is advanced and retracted by the driving of the driving unit 210, so the insertion unit can be inserted into a tissue of a patient or drawn out from the tissue. The driving unit 210 may include a solenoid, a linear actuator using a hydraulic/pneumatic cylinder, etc.

The insertion unit 320 is an element inserted up to a tissue through a tissue surface as described above, and is provided in the handpiece 200. The insertion unit 320 of the present embodiment includes a plurality of micro needles capable of being easily inserted into a tissue. In addition, the insertion unit may have various structures, such as a singular needle structure and a catheter. The micro needle of the present embodiment may be a needle having a diameter of a range of several to several thousands of μm. A needle having a diameter of a range of 10 to 1000 μm may be preferably used as the micro needle.

The insertion unit 320 is an element inserted into a tissue within the body of a patient and may have a sanitary problem if it is repeatedly used. Accordingly, the insertion unit of the present embodiment is provided within a tip module detachably provided at the end of the handpiece and is configured to be replaced after treatment.

Specifically, the tip module 300 is configured to include the insertion unit having the plurality of needles, and is detachably positioned in a handpiece body 201. Specifically, a base 301 forms the bottom of the tip module. Detachment protrusions 307 that are protruded outward are formed on the outer wall of the base. Guide grooves 241 guiding the detachment protrusions and an anti-separation groove 242 for preventing the detachment protrusions 307 guided along the guide grooves 241 from being separated are formed in a recess part 240 to which the tip module is coupled on the handpiece side. Furthermore, the detachment protrusions 307 of the tip module are disposed in the handpiece in such a manner that they are guided into the guide grooves 241 and coupled to the anti-separation groove 242. In this case, as in the present embodiment, an example in which the tip module is detachably positioned in the handpiece is illustrative, and the tip module or the insertion unit may be integrated with the handpiece.

Figure 3:
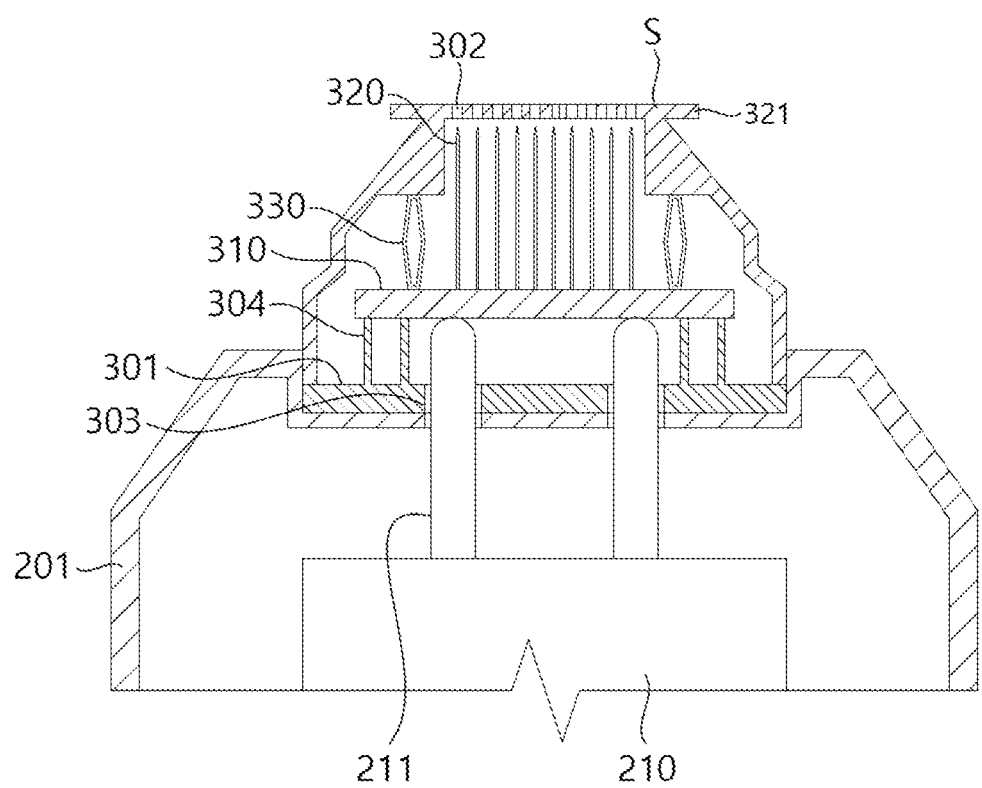
FIG. 3 is a cross-sectional view of the end of the handpiece of FIG. 2.

FIG. 3 is a cross-sectional view of the end of the handpiece of FIG. 2. Referring to FIG. 3, the front S of the end of the handpiece 200 is a portion that comes into contact with a skin tissue for treatment. A support plate 310 in which the insertion unit 320 is positioned is provided within the tip module 300. The plurality of needles 320 forming the insertion unit is fixed and disposed in the support plate 310 in a matrix form. RF energy is transferred through a circuit formed in the support plate 310. The front S of the tip module may form a portion that neighbors or comes into contact with the skin of a patient upon treatment. A plurality of advancing and retracting holes 302 through which the plurality of needles advances and retracts is formed in the front S.

At least one hole 303 through which the output terminal 211 can pass is provided at the bottom of the tip module. The output terminal 211 pressurizes the support plate 310 while linearly moving along the hole 303 when the driving unit 210 operates. The back of the support plate 310 is seated in a support 304 within the tip module, and the front thereof is pressurized by an elastic member 330 positioned within the tip module. When the output terminal 211 moves and pressurizes the support plate 310, the support plate 310 is separated from the support 304 and advances. Accordingly, the plurality of needles 320 is protruded toward the front of the hole 302 and inserted into a skin tissue. Furthermore, when the output terminal 211 is retracted by the driving of the driving unit 210, the support plate 310 is retracted by the restoring force of the elastic member 330, so the plurality of needles 320 also returns to the inside of the tip module. Although not separately shown, a separate guide member for guiding the path along which the support plate moves may be further provided.

Although not shown in the drawing specifically, the circuit of the support plate 310 may be configured to be electrically connected to the RF generator of the main body when the tip module is positioned in the handpiece. Alternatively, the circuit of the support plate may be configured to be selectively electrically connected to the RF generator when the support plate is pressurized by the output terminal 211 (e.g., an electrode may be formed at the end of the output terminal and electrically connected to the support plate when the support plate is pressurized).

Figure 4:
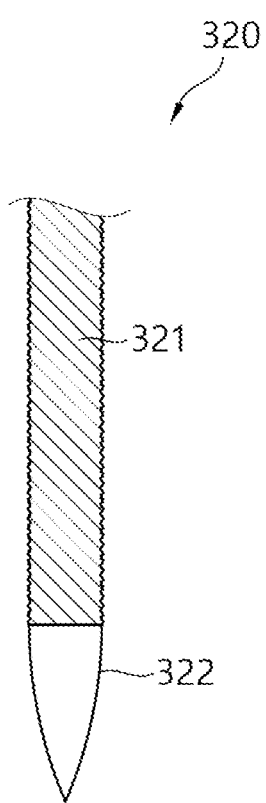
FIG. 4 is a cross-sectional view showing a cross section of one of a plurality of needles of FIG. 3.

FIG. 4 is a cross-sectional view showing a cross section of one of the plurality of needles of FIG. 3. Each of the needles 320 corresponding to the insertion unit may include a micro needle having a diameter of approximately 5 to 500 μm. The needle 320 is made of a conductive material in order to transfer RF energy. A portion of a surface of each needle except a tip is made of an insulating material 321 and is configured to not transfer RF energy to a tissue. Accordingly, a portion of the tip of each needle is configured to function as an electrode 322 and transfer RF energy to a tissue through the tip. Accordingly, during treatment, RF energy may be selectively transferred to a portion where the end of the needle is positioned.

Description is given basically with reference to FIGS. 1 and 2. The treatment apparatus 1 according to the present invention may further include a substance storage unit 400 for transferring a substance to a tissue during treatment. The substance storage unit is an element for receiving various substances used for tissue treatment. As shown in FIG. 2, the substance storage unit 400 is positioned on one side of the handpiece 200 through which the insertion unit 320 advances and retracts. That is, the substance storage unit 400 is positioned on the path along which the insertion unit advances and retracts. The insertion unit 320 penetrates the substance storage unit 400 while it performs an advancing and retracting operation. Accordingly, the substance of the substance storage unit may be transferred into a tissue by the insertion unit 320 during the advancing and retracting operation of the insertion unit.

Figure 5:
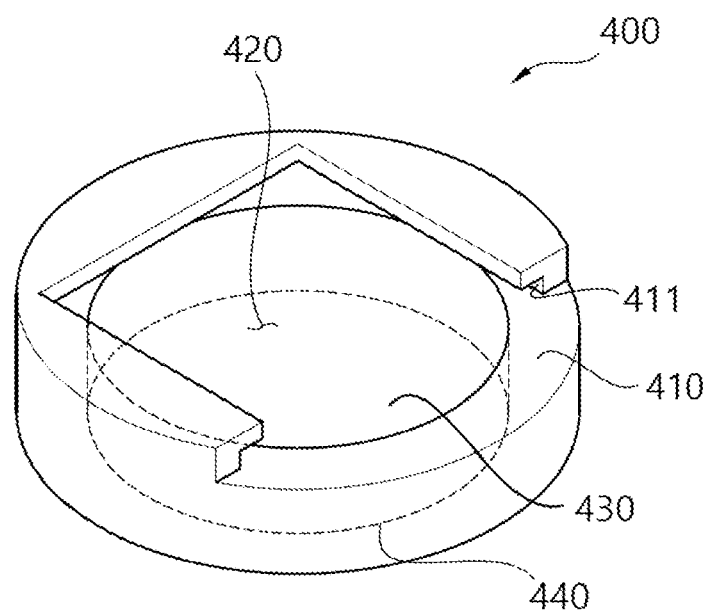
FIG. 5 is a cross-sectional view showing a cross section of a substance storage unit of FIG. 2.

FIG. 5 is a cross-sectional view showing a cross section of the substance storage unit of FIG. 2. As shown in FIG. 5, the substance storage unit 400 may include a case 410 and an accommodation space 420 provided within the case to receive a substance.

The substance received in the accommodation space 420 is a substance used for treatment, and may include a substance used for treatment as various objects, such as anesthesia, pain relief and side effect prevention, in addition to a substance having its own treatment effect. For example, the substance may be a substance including a bio substance, collagen, and anesthetic drugs, such as drugs and cells. Such a substance may have a viscous substance state, such as a gel, so that it can be easily applied on an external surface of the insertion unit 320 and transferred to a tissue while the insertion unit 320 passes. Alternatively, the substance may be configured in the state in which it is received by a support structure (e.g., a honeycomb structure (not shown)) formed within the accommodation space. The support structure may include a flexible structure that does not affect the advancing and retracting operation of the insertion unit.

A coupling structure to be selectively coupled to the handpiece may be configured on an external surface of the case 410. For example, in the present embodiment, the substance storage unit 400 is positioned to be selectively detachably in the tip module 300 of the handpiece. Specifically, a guide rib 321 is provided on the front of the tip module 300 of FIG. 2. A guide groove 411 to be coupled to the guide rib may be provided on an external surface of the case of the substance storage unit 400. Accordingly, the substance storage unit 400 is positioned in such a way as to slide on the front of the tip module 300. The handpiece may transfer a substance to a tissue when invasive treatment is performed.

As described above, in the treatment apparatus 1 according to the present invention, the substance storage unit 400 may be selectively positioned, if necessary, in order to perform invasive treatment in which only RF energy is transferred or to perform both RF energy transfer measurement and substance transfer treatment.

In this case, FIG. 2 shows an example in which the substance storage unit is positioned at the front end of the tip module, but this is an example. In addition, the substance storage unit may be changed and practiced in various manners. For example, the tip module and the substance storage unit may be configured into a single module and coupled to the handpiece at once. Alternatively, the substance storage unit may be configured to be coupled to the body of the handpiece not the tip module.

Meanwhile, as shown in FIG. 5, a pair of through surfaces 430 and 440 through which the insertion unit consisting of the micro needles penetrates is formed on the top and bottom (with respect to the drawing) of the substance storage unit 400. The through surface may be formed of a thin membrane structure made of a material having a viscoelasticity characteristic. For example, the through surface may be made of a polymer substance having a viscoelasticity characteristic. In this case, the insertion unit can easily penetrate the through surfaces. The through surfaces are configured to minimize the leakage of a substance within the accommodation space through a through hole (not shown) through which the insertion unit penetrates while the advancing and retracting operation of the insertion unit are repeatedly performed.

Moreover, although not shown in FIG. 5, the substance storage unit 400 may further include a separate marking part for indicating whether the substance storage unit is used. The marking part may be implemented in various manners, and may be configured to indicate whether the substance storage unit is used in such a way as to remove a sticker or packing materials or to indicate whether the substance storage unit is used in such a manner that part of the color of the through surface is changed when the through hole is penetrated. Accordingly, a sanitary problem, such as infection, can be prevented and a treatment effect can be guaranteed because the reuse of the substance storage unit is prevented.

Figure 6:
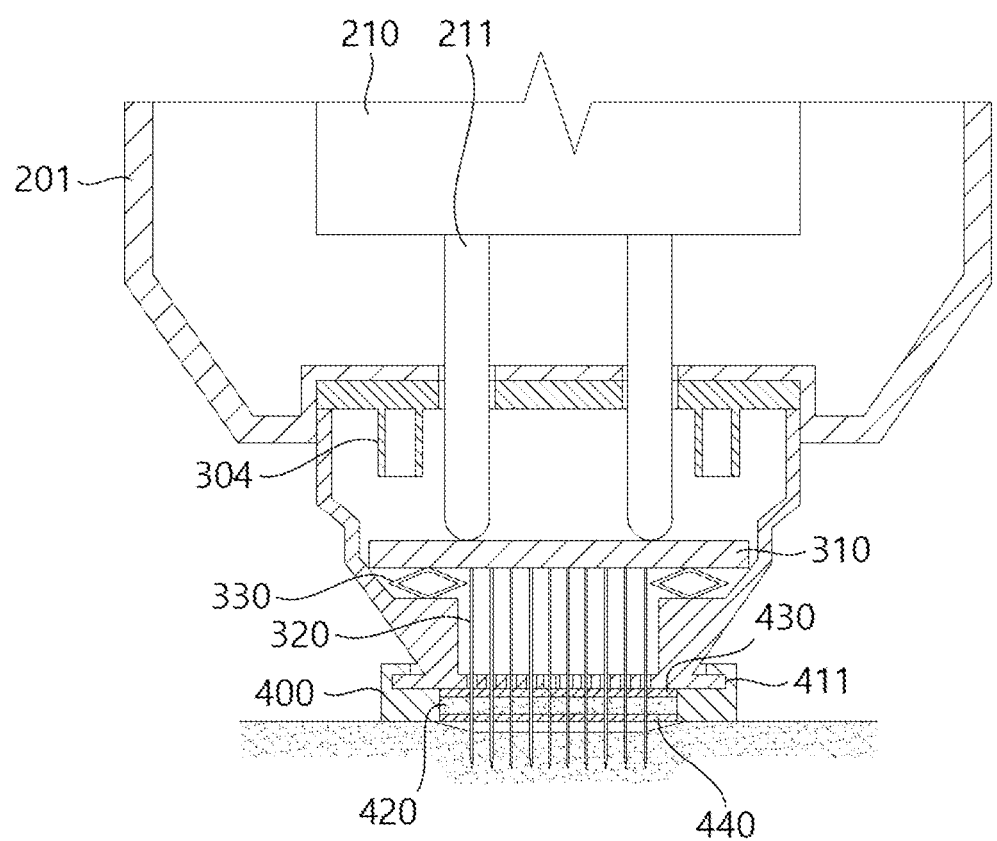
FIG. 6 is a diagram showing the state in which treatment has been performed in the state in which the substance storage unit has been installed in FIG. 1.

FIG. 6 is a diagram showing the state in which treatment has been performed in the state in which the substance storage unit has been installed in FIG. 1. As shown in FIG. 6, when the insertion unit 320 is advanced by the driving of the driving unit 210, the insertion unit 320 is inserted into a tissue through the substance storage unit 400. At this time, the insertion unit 320 is inserted into the tissue in the state in which a substance of the substance storage unit has been applied on an external surface of the insertion unit 320. The substance is transferred from the tissue surface to a target depth into which the end of the insertion unit is inserted along the insertion path of the insertion unit. Accordingly, treatment using RF energy and treatment using the substance can be performed at each treatment location at the same time.

The substance transferred along the insertion path may be a substance having the effect of improving skin lesions, such as wrinkle, skin elasticity and pigmentation, a substance having the effect of recovering wound through invasive treatment, a substance for reducing pain when invasive treatment is performed, or a substance having then effect of decomposing a subcutaneous fat tissue.

Furthermore, an external surface of the insertion unit 320 may have a surface-processed structure so that fine prominences and depressions are formed on the surface in order to improve transfer efficiency of a substance to a tissue (refer to FIG. 4). In this case, if the prominence and depression structure is sharp and large in size, a tissue may be damaged in a tissue insertion step. In the present embodiment, a coating surface of the insulating part 321 of the insertion unit may be subjected to surface processing and used.

Figure 7:
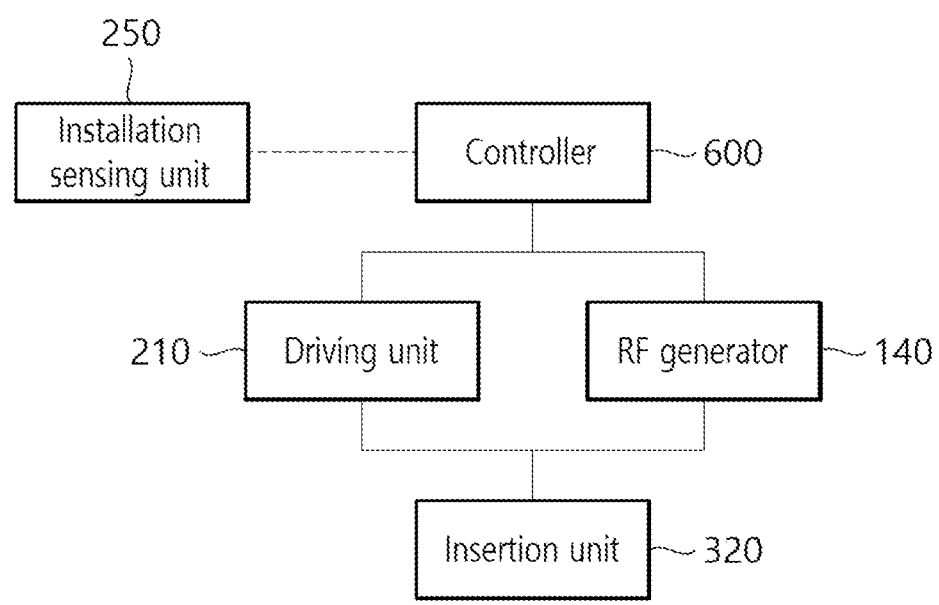
FIG. 7 is a block diagram showing major control systems of the treatment apparatus of FIG. 1.

FIG. 7 is a block diagram showing major control systems of the treatment apparatus of FIG. 1. As shown in FIG. 7, a controller 600 is an element controlling the operations of various elements of the main body and the handpiece. The controller may perform a treatment operation of the treatment apparatus by driving the RF generator 140 and the driving unit 210. The controller 600 controls a treatment operation based on a user's control or a preset mode. The controller 600 may further include a separate database or processor. Accordingly, when a variety of types of information necessary for control is transmitted to the controller, the controller may derive a suitable control signal based on the information by using or calculating previously stored data.

The controller 600 may control a treatment operation in a different mode depending on the location where the substance storage unit 400 is positioned in controlling the treatment operation of the treatment apparatus. For example, the controller 600 may control a treatment operation in a first mode in the state in which the substance storage unit has not been installed, and may control a treatment operation in a second mode in the state in which the substance storage unit has been installed. In this case, the first mode and the second mode are configured to have different treatment operations according to the insertion unit. For example, when the insertion unit performs an advancing and retracting operation, an advancing length or retracting length, the time taken for the advancing and retracting operation, the parameter of RF energy transferred through the end of the insertion unit, etc. may be differently configured. Such control contents are described more specifically with reference to FIG. 8 below.

Meanwhile, the controller 600 may determine whether the substance storage unit has been installed based on a signal input by a user. In the present embodiment, however, an installation sensing unit 250 for sensing whether the substance storage unit has been installed may be separately included. Although the configuration of the installation sensing unit is not specifically shown in FIGS. 1 and 2, the installation sensing unit may include a photosensor, a pressure sensor or a current-carrying sensor and may be easily configured to automatically sense the substance storage unit when it is positioned at the front of the handpiece or a location near the handpiece. Furthermore, the controller 600 may control a treatment operation in a treatment mode depending on whether the installation sensing unit has been installed based on information sensed by the installation sensing unit 250.

Alternatively, the controller 600 may perform control based on a treatment mode input by a user. If a control command not matched with information sensed by the installation sensing unit is received (e.g., a user inputs the first mode operation in the state in which the substance storage unit has been installed), the controller 600 may be configured to notify a user of the mismatching through the display unit.

Figure 8:
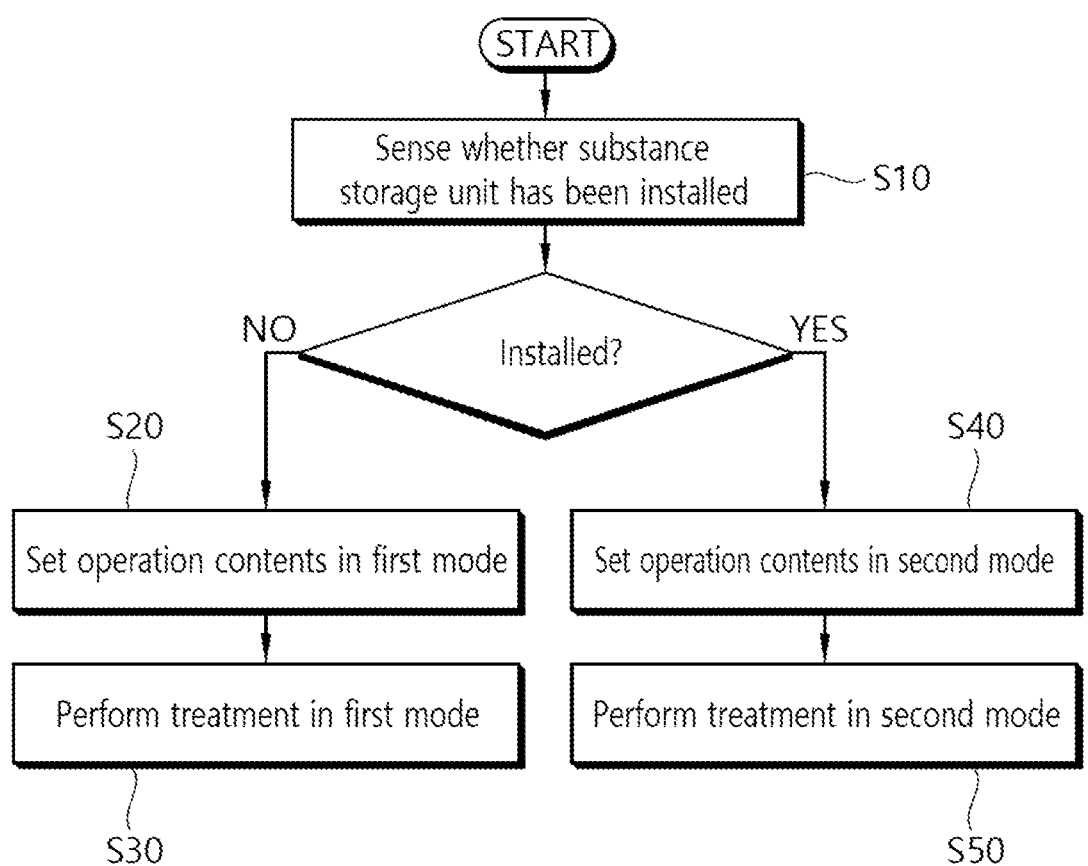
FIG. 8 is a flowchart showing a method of controlling the treatment apparatus of FIG. 1.

FIG. 8 is a flowchart showing a method of controlling the treatment apparatus of FIG. 1. The method of controlling the treatment apparatus of the present embodiment is described below with reference to FIG. 8.

Prior to the execution of treatment, the controller 600 senses whether the substance storage unit has been installed through the installation sensing unit 250 (S10). If it is determined that the substance storage unit has not been positioned, the controller 600 sets operation contents so that the treatment apparatus may operate in the first mode (S20). Furthermore, if it is determined that the substance storage unit has been installed, the controller sets operation contents so that the treatment apparatus operates in the second mode (S40). Furthermore, the controller performs treatment based on each mode (S30, S50).

Figure 9:
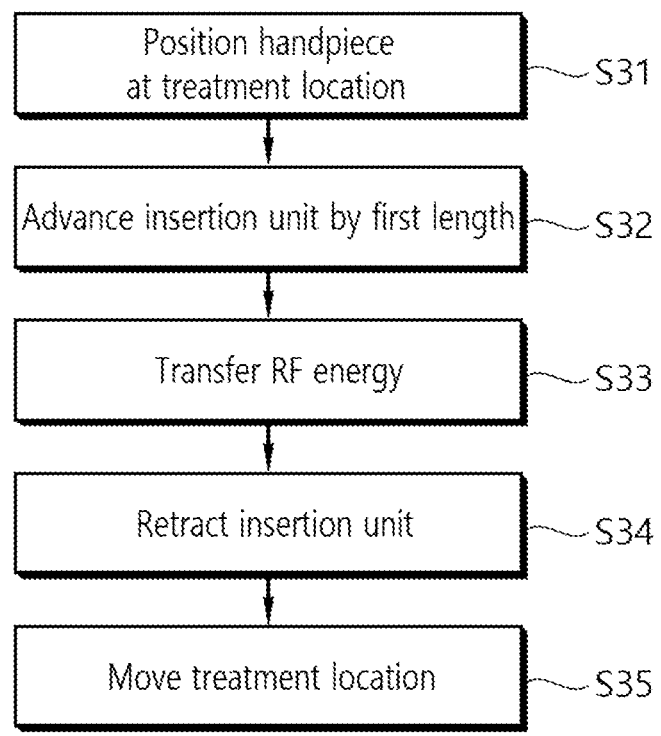
FIG. 9 is a flowchart showing steps according to a first mode in FIG. 8.

FIG. 9 is a flowchart showing treatment execution steps according to the first mode in FIG. 8. The treatment step S30 according to the first mode is treatment in which RF energy is transferred to the inside of a tissue without using separate drug transfer treatment.

First, the handpiece is positioned at the treatment location of a tissue (S31). At this time, the front end of the tip module of the handpiece is positioned to neighbor or come into contact with a tissue surface corresponding to the treatment location.

Furthermore, the driving unit 210 of the handpiece is driven to advance the insertion unit 320 of the handpiece 200 by a first length (S32). In this case, the first length is the distance for reaching up to the depth of a target location within the tissue in the state in which the substance storage unit has not been installed. For example, the first length may be the sum of the distance from the initial location of the end of the insertion unit to the end of the tip module coming into contact with a surface of the tissue and the depth from the tissue surface to the target location. Moreover, the first length may be a length to which a compensation length for compensating for displacement occurring from a surface of the tissue due to the insertion unit has been added.

When the end of the insertion unit 320 reaches up to the depth of the target location through the aforementioned step, RF energy is transferred to the target location (S33). Through this step, the RF energy generated from the RF generator 140 is transferred to the target location through the electrode of the end of the insertion unit, so treatment at the target location may be performed. This step is performed during a first time, and the RF energy may be transferred as a first output.

When the treatment step is terminated, the driving unit of the handpiece is driven to retract the insertion unit of the handpiece, thereby removing the insertion unit from the tissue (S34). Furthermore, the treatment location may be changed (S35), and steps S31 to S34 may be repeatedly performed.

Figure 10:
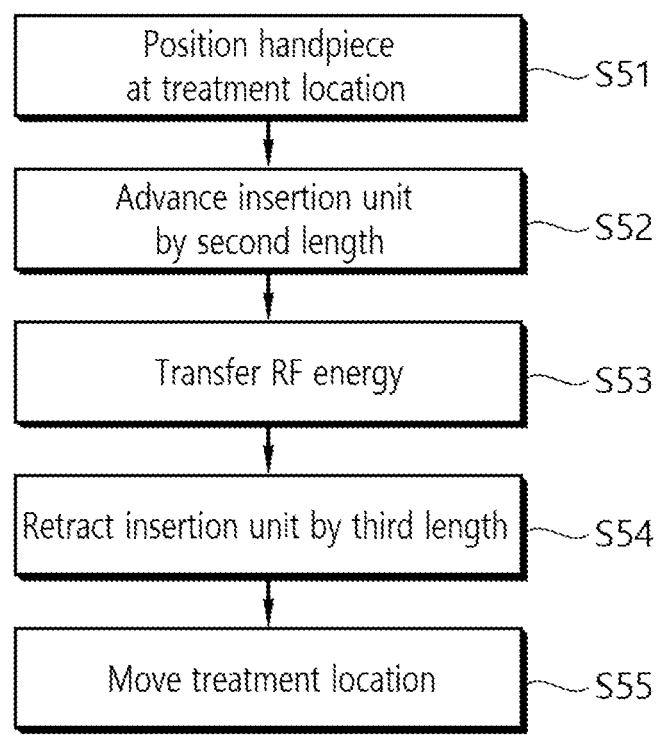
FIG. 10 is a flowchart showing steps according to a second mode in FIG. 8.

FIG. 10 is a flowchart showing treatment execution steps according to the second mode in FIG. 8. In the treatment step S50 according to the second mode, RF energy transfer treatment and substance transfer treatment for a tissue are performed at the same time in the state in which the substance storage unit 400 has been coupled.

As in the steps according to the first mode, the handpiece is positioned at the treatment location of a tissue (S51). Furthermore, the driving unit of the handpiece is driven to advance the insertion unit 320 of the handpiece by a second length (S52). In this case, the second length is the distance for enabling the end of the insertion unit to arrive from an initial location to a depth up to a target location within the tissue in the state in which the substance storage unit has been installed. Accordingly, the second length is greater than the first length and may be a value to which a length corresponding to the thickness of the substance storage unit has been added compared to the first length. In this case, the length corresponding to the thickness of the substance storage unit is not limited to the same length as the thickness, but may be construed as being an additional advancing length necessary due to the installation of the substance storage unit. Moreover, like the first length, the second length may be a length to which a compensation length for compensating for displacement occurring from a surface of the tissue due to the insertion unit has been added.

In this step, while the insertion unit penetrates the substance storage unit, a substance of the substance storage unit 400 is applied on the insertion unit along an external surface of the insertion unit 320 (refer to FIG. 6). Furthermore, while the insertion unit is inserted into the tissue through the substance storage unit, the substance applied on the external surface of the insertion unit is transferred from a tissue surface of a corresponding location to the depth of the target location along the insertion path.

When the end of the insertion unit reaches up to the depth of the target location through the aforementioned step, RF energy is transferred to the target location (S53). This step is performed for a second time, and the RF energy may be transferred as a second output. In this step, the RF energy is transferred in the state in which the substance has been transferred to the tissue. Parameters, such as the second time and the second output, may be set by taking into consideration an effect according to the substance. For example, if a substance includes a component capable of alleviating pain or a component that accelerates recovery, the second time may be set longer than the first time or the second output may be set greater than the first output so that sufficient RF energy can be transferred.

Thereafter, when the RF energy transfer step is terminated, the driving unit of the handpiece is driven to retract the insertion unit of the handpiece (S54). In this step, the insertion unit may be controlled to not retract up to the initial location (within the tip module) at steps S51 and S52, but to retract as much as the length that the insertion unit can be drawn out from the tissue. The retracting length of this step may be a third length smaller than the second length and may be the same as the retracting length in the operation according to the first mode. Through this step, the end of the insertion unit 320 may be located within the accommodation space 420 of the substance storage unit.

Thereafter, the treatment location may be changed (S55), and steps S51 to S54 may be repeatedly performed. In this case, the end of the insertion unit is different from the initial position at step S51 in the state in which the aforementioned step has been performed. Accordingly, in the step of advancing the insertion unit, the advancing length is controlled to be smaller than the second length. For example, the step of advancing the insertion unit may be repeatedly performed while advancing the insertion unit by the third length.

The treatment apparatus for performing treatment by transferring RF energy to a skin tissue has been chiefly described above. This is an example, and may be applied to a treatment apparatus that is focused on other tissue not a skin tissue. Furthermore, in the present embodiment, the treatment apparatus including the main body and the handpiece has been chiefly described, but the present invention is not limited thereto and may be applied to a treatment apparatus in which the handpiece is configured in a single module form.

Although one embodiment of the present invention has been described in detail, the present invention is not limited to the embodiment. It is to be noted that a person having ordinary skill in the art to which the present invention pertains may modify or change the present invention in various manners without departing from the scope of the technical characteristics of the present invention defined in the claims.

The invention claimed is:

1. A treatment apparatus, comprising:
   a handpiece;
   an RF generator generating RF energy;
   an insertion unit configured to advance and retract toward one direction of the handpiece, selectively inserted into a tissue, and electrically connected to the RF generator to transfer the RF energy to an inside of the tissue;
   a substance storage unit receiving a therapeutic substance therein and detachably installed on one side of the handpiece to transfer the substance to the inside of the tissue by the advancing operation of the insertion unit, and
   a controller controlling the advancing and retracting operation of the insertion unit,
   wherein an end of the insertion unit is inserted into the tissue when the insertion unit advances, and the end of the insertion unit is received within the substance storage unit when the retracting operation of the insertion unit is completed.

2. The treatment apparatus of claim 1, wherein:
   the substance storage unit is positioned on a path along which the insertion unit moves while the insertion unit performs the advancing and retracting operation, and
   the insertion unit is inserted into the tissue through the substance storage unit when performing the advancing operation.

3. The treatment apparatus of claim 2, wherein the insertion unit is inserted into the tissue in a state in which the substance has been applied on an external surface of the insertion unit while the insertion unit penetrates the substance storage unit.

4. The treatment apparatus of claim 1, wherein the substance is transferred from a surface of the tissue to a depth into which an end of the insertion unit is inserted along a path formed within the tissue by the insertion of the insertion unit.

5. The treatment apparatus of claim 1, wherein the insertion unit operates to transfer the RF energy after the substance is transferred to the inside of the tissue.

6. The treatment apparatus of claim 1, wherein an external surface of the insertion unit has a structure in which prominences and depressions are formed in order to improve transfer efficiency of the substance to the inside of the tissue.

7. The treatment apparatus of claim 1, wherein the controller differently controls the advancing and retracting operation of the insertion unit depending on whether the substance storage unit has been installed.

8. The treatment apparatus of claim 7, further comprising an installation sensing unit sending whether the substance storage unit has been installed, wherein the controller differently controls the advancing and retracting operation of the insertion unit based on information sensed by the installation sensing unit.

9. The treatment apparatus of claim 7, wherein:
   the controller controls the advancing and retracting operation of the insertion unit in a first mode in the state in which the substance storage unit has not been installed, and
   the controller controls the advancing and retracting operation of the insertion unit in a second mode in the state in which the substance storage unit has been installed.

10. The treatment apparatus of claim 8, wherein if a depth of a target location is identical, the insertion unit is additionally advanced as much as a length corresponding to a thickness of the substance storage unit in the second mode, compared to the first mode.

11. The treatment apparatus of claim 8, wherein:
   in the first mode, an end of the insertion unit is inserted into the tissue when the insertion unit advances, and the end of the insertion unit is received within the handpiece when the insertion unit retracts, and
   in the second mode, the end of the insertion unit is inserted into the tissue when the insertion unit advances, and the end of the insertion unit is received within the substance storage unit when the insertion unit retracts.

12. The treatment apparatus of claim 1, wherein the substance received in the substance storage unit has a gel form.

13. The treatment apparatus of claim 1, wherein at least one surface of the substance storage unit through which the insertion unit penetrates has a membrane structure having viscoelasticity so that the advancing and retracting operation of the insertion unit are performed and a leakage of the substance through a through hole formed by the advancing and retracting operation of the insertion unit is minimized.

14. The treatment apparatus of claim 1, wherein the substance storage unit further comprises a marking part indicating whether the substance storage unit is used when the substance storage unit is coupled to the handpiece.

15. The treatment apparatus of claim 2, wherein the insertion unit is inserted into the tissue in a state in which the substance has been applied on an external surface of the insertion unit without flowing into and through the insertion unit while the insertion unit penetrates the substance storage unit.

* * * * *